United States Patent [19]

Khanna

[11] Patent Number: 4,629,693
[45] Date of Patent: Dec. 16, 1986

[54] SENSITIVITY IN FLUORESCENCE ASSAYS IN ICTERIC SAMPLES

[75] Inventor: Pyare Khanna, San Jose, Calif.

[73] Assignee: Syntex (U.S.A.) Inc., Palo Alto, Calif.

[21] Appl. No.: 593,761

[22] Filed: Mar. 27, 1984

[51] Int. Cl.$^4$ .............. G01N 33/53; G01N 21/64; C12Q 1/00; C12Q 1/32

[52] U.S. Cl. .............. 435/7; 435/4; 435/26; 436/805

[58] Field of Search ............ 435/7, 4, 26; 436/805

[56] References Cited

U.S. PATENT DOCUMENTS 3,875,011 4/1975 Rubenstein et al. ............ 435/7 X
4,162,194 7/1979 Pierre et al. ............ 435/15
4,404,278 9/1983 Hu et al. ............ 435/7
4,565,790 1/1986 Hemmilä et al. ............ 436/537

OTHER PUBLICATIONS

*Clinical Biochemistry Principles and Methods*, Curtius et al., (Eds.) vol. 1, (1978), Walter de Gruyter, N.Y. pp. 250–251.

*Primary Examiner*—Robert J. Warden
*Assistant Examiner*—Patricia Kate White
*Attorney, Agent, or Firm*—Bertram I. Rowland; Theodore J. Leitereg; Carole F. Barrett

[57] ABSTRACT

Enhanced sensitivity in fluorescent assays employing NADH or NADPH is obtained, particularly in icteric samples, by employing excitation light at a wave length range below about 400 nm and reading emitted light above about 500 nm.

10 Claims, No Drawings

SENSITIVITY IN FLUORESCENCE ASSAYS IN ICTERIC SAMPLES

BACKGROUND OF THE INVENTION

1. Field of the Invention

An increasing variety of methods for detecting analytes are being developed, where most of the methods rely upon only a few different labels. These labels for the most part are radioactive nuclides, enzymes and fluorescers. Each of the labels brings to the assays advantages and problems associated with sensitivity, reproducibility, and interference resulting from components in the analyte sample. Frequently, when confronted within reproducible results or lack of correlation with other techniques, one of the major problems is determining the reason for the lack of correlation. Even after one has been able to isolate the reason for the interference, the solution to the problem may also be significantly complex.

2. Description of the Prior Art

*Enzyme Immunoassay*, ed, Edward T. Maggio, CRC Press, Boca Raton, Fla., 1980, U.S. Pat. Nos. 3,817,837, 3,875,011 and 4,091,613 are illustrative of enzyme immunoassays which produce nicotinamide adenine dinucleotide(NAD)-reduced form (NADH).

SUMMARY OF THE INVENTION

A method for detecting NADH or NADPH by fluorescence in assays involving icteric blood samples is provided by irradiating the sample with light below 400 nm and reading the emitted light above 500 nm.

DESCRIPTION OF THE SPECIFIC EMBODIMENTS

Enzyme immunoassays are provided for detecting the fluorescence of NADH and phosphorus derivatives thereof such as nicotinamide adenine dinucleotide phosphate(NADP)-reduced form (NADPH), where the amount of NADH or NADPH is related to the amount of analyte in an assay medium. The improvement comprises irradiating the assay medium with light at a wavelength below about 400 nm to excite the NADH or NADPH and reading the emitted light above about 500 nm. Preferably, the excitation light will be within the range of 340 to 390 nm, more preferably between about 345 to 375 nm, while the emitted light which is detected will be in the range of about 500 to 550 nm, more usually in the range of about 510 to 530 nm.

The invention may be used in any assay applied to icteric blood samples, which assay involves the fluorescent detection of either the formation or destruction of NADH or NADPH. The assay may be "homogenous" (not involving a separation step between label bound to a ligand-receptor complex and unbound label) or heterogeneous (involving a separation between the complex bound and unbound ligand). For the most part, these assays will involve the use of catalysts, particularly enzyme catalysts, where NAD, NADH, NADP or NADPH is a cofactor. Illustrative of such enzyme systems involving NADH are U.S. Pat. Nos. 3,875,011, 4,318,980 and 4,318,983, whose disclosures are incorporated herein by reference. U.S. Pat. No. 4,220,722 describes the production of NADH in an enzyme immunoassay employing aminoglycoside antibiotics in conjugation with glucose-6-phosphate dehydrogenase. The disclosure of this patent is also incorporated herein by reference.

Enzymes which employ NAD or NADP as a cofactor include glucose-6-phosphate dehydrogenase, malate dehydrogenase, lactate dehydrogenase, alcohol dehydrogenase, glyoxylate reductase, mannitol-1-phosphate dehydrogenase, etc.

As illustrative of methods involving the production of NADH in an assay employing enzyme labels, the method of U.S. Pat. No. 4,220,722 is employed. The method is performed in an aqueous buffered medium, generally at a pH in the range of about 5–10, more usually 6–9. Usually, one combines the sample to be assayed, enzyme-bound-ligand (ligand is the analyte or an analog thereof which has analogous immunological specificity) and antiligand (a macromolecular receptor which specifically binds to the ligand or ligand analog and is usually an antibody or naturally occurring receptor). Besides water, up to 40 volume percent of a polar organic solvent, such as alkanols, ethers, and amides, or the like may be included in the assay medium.

The amounts of the reagents employed will vary depending upon the enzyme activity of the enzyme-bound-ligand, the degree of inhibition resulting from binding of antiligand to the enzyme-bound-ligand, the sensitivity of the instrumentation, the binding constant of the antiligand, and the like. Over the range of concentration of interest of the ligand, desirably, there should be at least about a 20% change in fluorescence from the maximum fluorescence observed.

Usually, the molar ratio of antiligand based on binding sites to ligand in enzyme-bound ligand will be about 0.01–100:1. The concentration of enzyme-bound-ligand will generally be in the range of about $10^{-5}$–$10^{-10}$ moles per liter.

Included in the assay medium will be the enzyme substrates in addition to the NAD or the NADH. By taking two readings at a particular wavelength over a predetermined time period, a rate value can be obtained which relates to the enzymatic activity. By employing the same protocol with an unknown sample as compared with samples containing known concentrations of ligand, the result obtained can be translated into a ligand concentration.

Temperatures for the assay will generally be in the range of about 10°–50° C., usually in the range of about 25°–40° C. During the rate study, the medium will normally be thermostatically controlled.

Any kind of fluorometer may be employed which provides for irradiation at the appropriate wavelength and detection of the emitted light above 500 nm. Of particular interest is the instrument, Advance ®, sold by Syva Company, Palo Alto, Calif.

The analyte may be any organic ligand or receptor including haptens, e.g., drugs, hormones, steroids, alkaloids, oligopeptides, saccharrides, etc; antigens, e.g., polypeptides, glycoproteins, proteoglycans, polysaccharrides, e.g., neuramic acids, etc.; nucleic acids; receptors, e.g., antibodies, surface membrane receptors, lectins, etc., or the like.

The following is a particular example of an assay method in accordance with the present invention by way of illustration and not limitation. A number of reagent solutions are prepared having the following formulation:

Basic Buffer 0.055M Tris-HCl 0.05% NaN$_3$
0.005% Thimerosal
pH 8.1 at room temperature Assay Buffer Basic Buffer
0.5% NaCl
0.01% Triton X-100
pH 8.1 at room temperature Substrate/Antibody Diluent Basic Buffer
1.0% rabbit serum albumin (RSA)
0.4M nicotinamide adenine dinucleotide (NAD) in H$_2$O
0.066M glucose-6-phosphate (G6P)
pH 5.0 at room temperature Enzyme Diluent Basic Buffer
1.0% RSA
0.9% NaCl
pH 8.1 at room temperature Substrate/Antibody Reagent A Substrate/Antibody Diluent is used to dilute gamma-globulin containing antiligand, so that about 86% of the enzyme activity of glucose-6-phosphate dehydrogenase-ligand conjugate activity is inhibited in the assay medium.

Enzyme Reagent B

The enzyme-ligand conjugate is diluted with enzyme diluent to attain the desired maximum rate. This is measured by aspirating into a fluorometer and taking the change in readings with irradiation at 355 nm and reading at 520 nm over a 20 sec. period (12.5 reading/sec.) with a 9 sec. delay.

In carrying out the assay, the assay solution is prepared by combining the following: 50 µl of the sample to be assayed, 50 µl of Reagent A, and 50 µl of Reagent B with 70 µl of assay buffer, where portions of the assay buffer may be mixed with the reagents to facilitate transfer. The mixture is then aspirated into the fluorometer and the readings taken as indicated above. The concentration of the ligand is determined from a standard curve prepared by carrying out the assay using standardized solutions and taking readings.

In the following specific experiments icteric blood samples are spiked with 15 µg/ml of amikacin, where the icteric nature of the blood sample is related to the amount of bilirubin in the sample. The results are reported as the percent recovery when detecting the emitted light at 470 nm and 520 nm. The common wavelength range employed is 470 nm since it is about at the emission peak of NADH, where the slope of the emission curve is relatively flat. By contrast, 520 nm is at a wavelength where the slope of the emission curve is relatively steep and the rate of change of the observed emission level changes rapidly with change in wavelength.

The amount of the amikacin is determined by relating the observed percent emission to standard curves prepared employing known amounts of amikacin and fitting a curve to the change in percent emission with amikacin concentration. The following Table relates the icteric blood samples to the concentration of bilirubin in the sample and reports the percent recovery, that is, the value of amikacin reported based on the percent fluorescence as compared to the actual amount of amikacin introduced into the sample.

TABLE 1

| Blood Sample Type | | % recovery | |
| --- | --- | --- | --- |
| Icteric | Bilirubin mg/dl | 470 nm | 520 nm |
| | trace | 100 | 100 |
| | 5 | 90.2 | 98 |
| | 10 | 80.5 | 95 |
| | 20 | 64.4 | 89 |
| | 40 | 42.6 | 80 |

It is evident from the above results that in icteric blood samples substantial improvement in the observed results can be achieved by detecting the emitted light from NADH above 500 nm, rather than below 500 nm. Thus, more accurate determinations can be made of the amount of drug in an icteric sample.

Although the foregoing invention has been described in some detail by way of illustration and example for purposes of clarity of understanding, it will be obvious that certain changes and modifications may be practiced within the scope of the appended claims.

What is claimed is:

1. In an enzyme immunoassay method for the determination of an analyte in an icteric blood sample suspected of containing said analyte, said method comprising combining in an assay medium said sample and assay reagents and irradiating said medium, said method involving the production or oxidation of NADH or NADPH in said medium and employing fluorescent detection of NADH or NADPH wherein a change in fluorescence is related to the amount of analyte in said sample, the improvement which comprises irradiating said medium containing said sample and said assay reagents with light below 400 nm to excite NADH or NADPH produced or oxidized in said assay medium and detecting the fluorescence of NADH or NADPH at a wavelength at or above 500 nm.

2. The method of claim 1 wherein said method involves employing in said assay medium glucose-6-phosphate dehydrogenase, glucose-6-phosphate and NAD or NADP and wherein said glucose-6-phosphate dehydrogenase is employed as a catalyst and reacts with said glucose-6-phosphate and as a result thereof said NADH or NADPH is produced.

3. The method of claim 1 wherein said assay method involves the measurement of a hapten.

4. The method of claim 1 wherein said method is a homogeneous assay.

5. The method of claim 1 wherein said method involves employing in said assay medium a dehydrogenase, a substrate for said dehydrogenase, and NAD or NADP and wherein said dehydrogenase is employed as a catalyst and reacts with said substrate and as a result thereof said NADH or NADPH is produced.

6. In an enzyme immunoassay method for the determination of an analyte in an icteric blood sample suspected of containing said analyte, said method comprising combining in an assay medium said sample and assay reagents and irradiating said medium, said method involving employing in said assay medium an enzyme, a substrate for said enzyme, and employing NAD or NADP as a cofactor for said enzyme, said method involving production of the reduced form of NAD or NADP in said medium and employing detection of the reduced form of NAD or NADP in said medium by measuring the light emitted by said reduced form of NAD or NADP, the improvement which comprises irradiating said assay medium containing said sample and said assay reagents suspected of containing said reduced form of NAD or NADP with light below about 400 nm and measuring the light emitted by said reduced form at a wavelength at or above 500 nm.

7. The method of claim 6 wherein the enzyme is glucose-6-phosphate dehydrogenase.
8. The method of claim 6 wherein the assay is for a hapten.
9. The method of claim 6 which is a homogeneous assay method.
10. The method of claim 6 wherein the enzyme is a dehydrogenase.

* * * * *